United States Patent
Farrell et al.

(10) Patent No.: US 11,951,219 B2
(45) Date of Patent: Apr. 9, 2024

(54) METHOD FOR STERILIZING A SUBSTRATE HAVING A HYDROPHILIC COATING AND STERILIZED SUBSTRATES

(71) Applicant: Hollister Incorporated, Libertyville, IL (US)

(72) Inventors: David J. Farrell, Ballina (IE); John P. O'Mahony, Ardnacrusha (IE)

(73) Assignee: Hollister Incorporated, Libertyville, IL (US)

( * ) Notice: Subject to any disclaimer, the term of this patent is extended or adjusted under 35 U.S.C. 154(b) by 1278 days.

(21) Appl. No.: 16/478,543

(22) PCT Filed: Jan. 19, 2018

(86) PCT No.: PCT/US2018/014360
§ 371 (c)(1),
(2) Date: Jul. 17, 2019

(87) PCT Pub. No.: WO2018/136703
PCT Pub. Date: Jul. 26, 2018

(65) Prior Publication Data
US 2020/0038529 A1    Feb. 6, 2020

Related U.S. Application Data

(60) Provisional application No. 62/448,733, filed on Jan. 20, 2017.

(51) Int. Cl.
*A61L 2/08*    (2006.01)
*A61M 25/00*    (2006.01)
(Continued)

(52) U.S. Cl.
CPC .............. *A61L 2/087* (2013.01); *A61L 2/081* (2013.01); *A61M 25/002* (2013.01);
(Continued)

(58) Field of Classification Search
CPC ...... A61L 2/087; A61L 2/081; A61L 2202/18; A61L 2202/24; A61M 25/002; A61M 2025/0019; A61M 2205/0238; C10M 107/28; C10M 107/42; C10M 2209/0863; C10M 2217/0285
See application file for complete search history.

(56) References Cited

U.S. PATENT DOCUMENTS 4,869,299 A * 9/1989 Handke ............... G21F 5/018
141/2
5,283,034 A    2/1994 Okrongly et al.
(Continued)

FOREIGN PATENT DOCUMENTS

EP    0152012 A2    8/1985
EP    1252898 A2    10/2002
(Continued)

OTHER PUBLICATIONS

International Search Report and Written Opinion of the International Searching Authority dated May 24, 2018 for International Application No. PCT/US2018/014360.

*Primary Examiner* — Jacob K Ackun
(74) *Attorney, Agent, or Firm* — Cook Alex Ltd.

(57) ABSTRACT

Methods for sterilizing a substrate with radiation and radiation sterilized substrates.

20 Claims, 2 Drawing Sheets

Sample C

Sample D

Sample E

Sample F

(51) Int. Cl.
  *C10M 107/28* (2006.01)
  *C10M 107/42* (2006.01)
  *C10N 40/00* (2006.01)
  *C10N 50/08* (2006.01)

(52) U.S. Cl.
  CPC ........ *C10M 107/28* (2013.01); *C10M 107/42* (2013.01); *A61L 2202/18* (2013.01); *A61L 2202/24* (2013.01); *A61M 2025/0019* (2013.01); *A61M 2205/0238* (2013.01); *C10M 2209/0863* (2013.01); *C10M 2217/0285* (2013.01); *C10N 2040/50* (2020.05); *C10N 2050/08* (2013.01)

(56) References Cited

U.S. PATENT DOCUMENTS

| | | |
|---|---|---|
| 5,789,018 A | 8/1998 | Engelson et al. |
| 5,968,807 A | 10/1999 | Kaiser et al. |
| 6,465,799 B1 | 10/2002 | Kimble et al. |
| 6,986,868 B2 | 1/2006 | Madsen |
| 7,833,475 B2 | 11/2010 | Madsen |
| 8,267,919 B2 | 9/2012 | Utas et al. |
| 8,377,498 B2 | 2/2013 | Rindlav-Westling et al. |
| 8,703,048 B2 | 4/2014 | Nielsen et al. |
| 8,740,863 B2 | 6/2014 | Nestenborg et al. |
| 8,968,648 B2 | 3/2015 | Kaneko |
| 8,986,265 B2 | 3/2015 | Nestenborg et al. |
| 9,028,858 B2 | 5/2015 | Nielsen et al. |
| 9,138,510 B2 | 9/2015 | Madsen |
| 11,376,110 B2* | 7/2022 | Fearnot ................ A61F 2/9522 |
| 2005/0137582 A1 | 6/2005 | Kull-Osterlin et al. |
| 2005/0214443 A1 | 9/2005 | Madsen |
| 2008/0110770 A1 | 5/2008 | Burke et al. |
| 2009/0306244 A1 | 12/2009 | Belt |
| 2010/0168864 A1* | 7/2010 | White ................... A61B 17/562 623/18.11 |
| 2010/0234681 A1* | 9/2010 | Knapp ................... A61B 50/30 600/37 |
| 2010/0249245 A1 | 9/2010 | Whiteley |
| 2012/0318685 A1 | 12/2012 | Utas et al. |
| 2014/0190846 A1 | 7/2014 | Belt |
| 2014/0271351 A1 | 9/2014 | Nielsen et al. |
| 2015/0065998 A1 | 3/2015 | Nielsen et al. |
| 2015/0068927 A1 | 3/2015 | McBurney et al. |
| 2015/0119978 A1* | 4/2015 | Tegels ................... A61F 2/2427 206/370 |
| 2015/0351888 A1* | 12/2015 | Zoll ..................... A61F 2/0045 606/151 |
| 2016/0263285 A1 | 9/2016 | Rostami et al. |
| 2016/0287757 A1 | 10/2016 | Belt et al. |
| 2016/0288940 A1 | 10/2016 | Belt et al. |
| 2016/0310642 A1 | 10/2016 | Clarke et al. |
| 2018/0344993 A1* | 12/2018 | Ganz ................. A61M 25/1011 |
| 2019/0290806 A1* | 9/2019 | Farrell .................. A61L 29/005 |
| 2020/0038529 A1* | 2/2020 | Farrell .................... A61L 2/087 |
| 2020/0054795 A1* | 2/2020 | Farrell ................ A61M 25/002 |

FOREIGN PATENT DOCUMENTS

| | | |
|---|---|---|
| EP | 1131112 B1 | 2/2003 |
| EP | 1961429 A2 | 8/2008 |
| EP | 1312385 B2 | 10/2009 |
| EP | 1888127 B1 | 1/2010 |
| EP | 1599248 B1 | 6/2010 |
| EP | 1420846 B1 | 12/2010 |
| EP | 2277554 A1 | 1/2011 |
| EP | 2102324 B1 | 6/2011 |
| EP | 1696990 B1 | 3/2012 |
| EP | 2515959 A1 | 10/2012 |
| EP | 2121044 B1 | 5/2013 |
| EP | 2303346 B1 | 9/2013 |
| EP | 2736546 A1 | 6/2014 |
| EP | 2065061 B1 | 3/2015 |
| EP | 2845619 A1 | 3/2015 |
| EP | 1852139 B1 | 5/2016 |
| EP | 2515988 B1 | 7/2016 |
| EP | 2198897 B1 | 8/2016 |
| WO | WO 90/00907 A1 | 2/1990 |
| WO | WO 2007/137699 A1 | 12/2007 |
| WO | WO 2015/069843 A2 | 5/2015 |
| WO | WO 2015/075141 A1 | 5/2015 |
| WO | WO 2015/075142 A1 | 5/2015 |
| WO | WO 2015/089181 A2 | 6/2015 |
| WO | WO 2016/168461 A1 | 10/2016 |

\* cited by examiner

Sample C

Sample D

Sample E

Sample F

METHOD FOR STERILIZING A SUBSTRATE HAVING A HYDROPHILIC COATING AND STERILIZED SUBSTRATES

RELATED APPLICATION

The present application is the U.S. National Stage Application of PCT Application No. PCT/US2018/014360, filed Jan. 19, 2018, which claims the benefit and priority of U.S. Provisional Patent Application No. 62/448,733, filed Jan. 20, 2017, both of which are hereby incorporated herein by reference.

TECHNICAL FIELD

The present disclosure generally relates to methods for sterilizing a hydrophilically coated substrates using radiation, and more particularly, methods for radiation sterilization of hydrophilic coatings including a hydrophilic polymer and a low molecular weight diacrylate. The methods may include contacting the hydrophilic coating of a medical device with an aqueous solution containing one or more non-polymeric polyols and then exposing the medical device to radiation. The present disclosure also relates to sterilized hydrophilically coated medical devices, such as urinary catheters, and more particularly to ready-to-use sterilized hydrophilically coated medical device assemblies that include a package having therein a hydrophilically coated medical device and an aqueous solution containing a non-polymeric polyol, wherein the hydrophilic coating includes a hydrophilic polymer and a low molecular weight diacrylate oligomer.

BACKGROUND

It is known to coat medical devices, such as urinary catheters, with a hydrophilic coating. When the hydrophilic coating is wetted or hydrated with a wetting fluid, such as water, it becomes extremely lubricous which eases introduction of the device into the body and aids in reducing pain and discomfort associated with such introduction.

In some applications, the hydrophilically coated medical device is provided in a "dry" state wherein the user is required to wet the hydrophilic coating with a wetting fluid immediately prior to insertion into the body. In other applications, it is desirable to provide a hydrophilically coated medical device that is in a ready-to-use condition right out of the package. In the field of urinary catheters, a hydrophilically coated catheter may be provided in a catheter package wherein the catheter is stored in the package in contact with water so that the hydrophilic coating is wetted within the package and the catheter is ready for use right out of the package for the end user.

For various reasons, including but not limited to efficiency, effectiveness and cost, it is desirable to radiation sterilize packaged medical device assemblies. In some instances, the hydrophilically coated medical device and water are placed in the package and the package is sealed. After the package is sealed, the package having the hydrophilically coated medical device and water therein is exposed to radiation, such as gamma or E-Beam radiation, to sterilize the medical device. It has been found, however, that sterilization of hydrophilic coatings in the hydrated state or while in contact with a wetting fluid can result in degradation of the coating or excessive crosslinking of the coating which can lead to an increase of coefficient of friction (decrease in lubricity) of the coating and/or cause instability of coating which may result in the coating undesirably detaching from the medical device prior to or during use.

Therefore, there remains a need for methods of sterilizing medical devices having hydrophilic coatings.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method for sterilizing a substrate, such as a medical device, having a hydrophilic coating that includes a hydrophilic polymer and a low molecular weight diacrylate compound wherein the method includes contacting the hydrophilic coating of the substrate with a wetting fluid containing one or more non-polymeric polyol and sterilizing the medical device by applying a sufficient amount of radiation while the device is in contact with the wetting fluid.

In another aspect, a catheter assembly includes a package defining a cavity. A medical device including a hydrophilic coating is located within the cavity wherein the hydrophilic coating includes a hydrophilic polymer and a low molecular weight diacrylate compound. The assembly also includes a wetting fluid comprising one or more non-polymeric polyols is located within the cavity and in contact with the hydrophilic coating.

DETAILED DESCRIPTION OF THE ILLUSTRATED EMBODIMENTS

Figure 1:
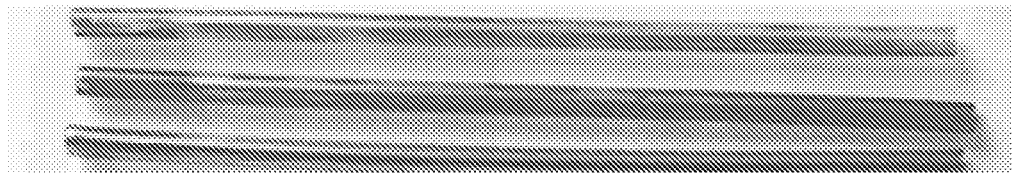
FIG. 1 includes photographs of catheter tubes showing the visual results of the dye tests of Example 2.
Figure 1:
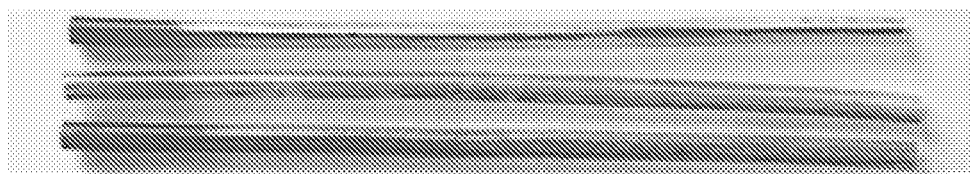
Figure 1:
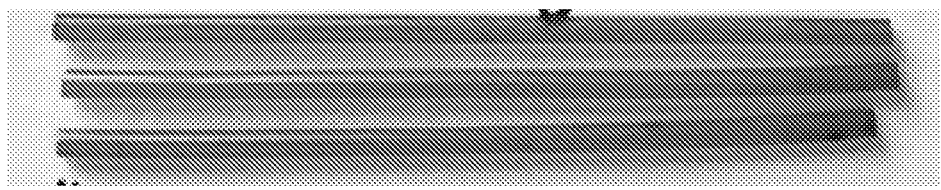
Figure 1:
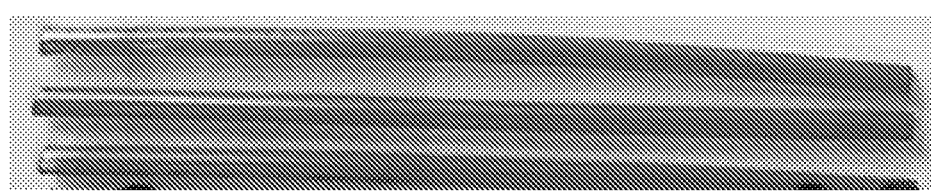

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure relates to methods for sterilizing hydrophilically coated substrates, such as medical devices, using radiation wherein the hydrophilic coatings include a hydrophilic polymer and a low molecular weight diacrylate compound, such as a diacrylate oligomer. In one embodiment the diacrylate compound is polyethylene glycol diacrylate (PEGDA). Such methods may include bringing the hydrophilic coating of the medical device into contact with a wetting fluid for wetting the hydrophilic coating wherein the wetting fluid includes a wetting agent, such as liquid water, and one or more non-polymeric polyols. The hydrophilically coated medical device is then sterilized by applying a sufficient amount of radiation, such as gamma or E-Beam radiation.

Surprisingly, it has been found that the coefficient of friction can be kept low and the stability of a hydrophilic coating containing a low molecular weight diacrylate compound and a hydrophilic polymer can be maintained by adding non-polymeric polyols to the liquid for wetting a hydrophilic coating and that the non-polymeric polyols protect these properties during exposure to radiation for sterilization when wetted with such wetting fluids. It has been found that in irradiation sterilized hydrophilically coated devices that the combination of a hydrophilic coating containing a low molecular weight diacrylate compound and the use of a wetting fluid containing non-polymeric polyols can increase the stability and attachment of the coating to the surface of the substrate.

In some instances of applying hydrophilic coatings, the surface of the substrate is treated prior to forming a hydrophilic coating on the surface. For example, the surface of a substrate of a urinary catheter may undergo a treatment, such as corona treatment, plasma treatment or the like or washing with a solvent, such ethanol or the like, to activate and/or clean the surface which can increase the affinity or attachment of the hydrophilic coating to the surface of the substrate. In other surface treatments, a primer or base layer is formed on the surface of the substrate wherein the primer or base layer acts a tie layer that has good attachment to both the surface of the substrate and of the hydrophilic surface.

Surprisingly, it has been found that a hydrophilic coating containing a low molecular weight diacrylate compound and a hydrophilic polymer can be formed directly on the surface of the substrate, without treating the surface of the substrate. It has also been found that when such a coating is applied directly to the substrate and is radiation sterilized while in contact with a wetting fluid containing one or more non-polymeric polyols that coating has a strong adhesion to the substrate and maintains structural integrity.

The non-polymeric polyols contained in the wetting fluid may be, for example, 3-carbon sugar alcohols (Glycerol); 4-carbon sugar alcohols (Erythritol, Threitol); 5-carbon sugar alcohols (Arabitol, Xylitol, Adonitol) sugar alcohols, 6-carbon sugar alcohols (Mannitol, Sorbitol, Galactitol, Fucitol, Iditol, Inositol), 7-carbon sugar alcohols (Volemitol), 12-carbon sugar alcohols (Isomalt, Maltitol, Lactitol), 18-carbon sugar alcohols (Maltotriitol), and 24-carbon sugar alcohols (Maltotetraitol). In one embodiment, the wetting fluid includes water and glycerol.

The disclosure also relates to sterilized assemblies that may include a hydrophilically coated medical device and a wetting fluid for wetting the hydrophilic coating wherein the wetting fluid includes one or more non-polymeric polyols, the hydrophilic coating includes a hydrophilic polymer and a low molecular weight diacrylate and the hydrophilic coating has been formed on a treated or untreated surface of the medical device. The assemblies having been sterilized with radiation while the hydrophilic coating is in contact with the wetting fluid.

In one embodiment, the sterilized assembly includes a hydrophilically coated medical device, such as a urinary catheter having a hydrophilic coating thereon, and a wetting fluid including one or more non-polymeric polyols wherein the coated medical device and the wetting fluid are located in a sealed package and the assembly is exposed to radiation to sterilize the assembly and the medical device therein. In this embodiment, the hydrophilic coating of the medical device is wetted within the package and is maintained in a wetted state within the package, such that the medical device is in a ready-to-use condition right out of the package. In one embodiment, the catheter may be positioned in a sleeve that contains wetting fluid and the sleeve may be the package or the sleeve may be placed in an outer package. The sleeve may be, for example, a no-touch sleeve wherein the user uses the sleeve to insert the catheter. Furthermore, the hydrophilic coating may include a hydrophilic polymer and a low molecular weight diacrylate and the coating may be formed on a treated or untreated surface. Additionally, the package may be made of a substantially liquid and gas impermeable material so as to substantially limit the amount of or prevent the wetting fluid from escaping the package during storage, which may prolong the shelf life of the assembly.

By using wetting fluids that include a non-polymeric polyol and a hydrophilic coating made a hydrophilic polymer and low molecular diacrylates, it is possible to provide a hydrophilically coated medical device, such as a hydrophilically coated catheter, that is maintained in a wetted state by a wetting fluid within a package and has been radiation sterilized. Such a medical device is in a ready-to-use state out of the package and includes a sufficiently low coefficient of friction and stability of the coating adhesion to the medical device, even in instances wherein the medical device and hydrophilic coating are stored in a wetting fluid for an extended period of time.

The wetting fluid may be a fluid that includes one or more non-polymeric polyols in the amount of from about 5 wt % to about 50 wt % of the wetting fluid. For example, the wetting fluid may include water and between about 10 wt % and about 20 wt % of a non-polymeric polyol, such as glycerol. In another embodiment, the amount of non-polymeric polyol may be about 5 wt % of the wetting fluid.

The wetting fluid, optionally, may contain other additives as well, such as antioxidants, which may be for example tocopherols (vitamin E) or ascorbic acid (vitamin C).

The hydrophilic coatings may be formed from a coating composition that includes a low molecular weight diacrylate compound, such as a diacrylate oligomer, and a hydrophilic polymer. The hydrophilic polymer may be polyvinylpyrrolidone (PVP), polyethylene oxide, methyl cellulose, ethyl cellulose, polyethylene glycol, hydroxyl methylcellulose, hydroxypropyl cellulose, hydroxypropyl methylcellulose, carboxymethyl cellulose, polyvinyl alcohol, or mixtures thereof. In one embodiment, the hydrophilic polymer is a polymer having a Mw above 500,000. For example, the hydrophilic polymer may be PVP having a Mw of at least 500,000. In one embodiment the diacrylate compound has a number average molecular weight (Mn) of less than about 1000 or less than about 900, preferably less than 600, more preferably between about 200 and about 600, and even more preferably between about 400 and about 600. The diacrylate compound may be, for example, PEGDA having a Mn of less than about 1000 or less than about 900. In one embodiment, the PEGDA has Mn of less than about 600. In another embodiment, the PEGDA has Mn of between about 200 and about 600. In yet another embodiment, the PEGDA has a Mn of between about 400 and about 600.

The present disclosure also discloses base coat and top coat compositions that may be used to form such hydrophilic coatings. The base coat and top coat compositions may be solutions or dispersions that are applied to the surface of a substrate, and then cured and/or dried to form the base coat and top coat layers of the hydrophilic coating. While the base coat and top coat compositions disclosed herein and coatings formed therefrom are described relative to urinary catheters, the compositions and coatings may be used to coat virtually any substrate for which it is desired to provide a lubricous hydrophilic coating on the surface thereof. The coatings and compositions are particularly useful for medical devices that are intended to be inserted into and removed from the body, such as urinary catheters, endoscopes, drainage catheters, etc.

The base coat compositions and top coat compositions disclosed herein may be used with one another to form lubricious hydrophilic coatings on a substrate. While the top coat compositions may be applied over the base coat compositions, a base coat is not required and the top coat compositions may be applied directly to the surface of the substrate to form a hydrophilic coating on the substrate. In one embodiment, the top coat composition may be applied directly to an untreated surface of a substrate. For example, the hydrophilic composition (top coat) may be applied directly to an untreated surface of a urinary catheter without the use of a base coat or wherein the surface has not been treated with plasma treatment, corona treatment or the like or with a solvent prior to application of hydrophilic composition which forms the hydrophilic coating.

Turning back the base coat, the base coat may be formed from a blend including a hydrophilic polymer and a diacrylate compound having a number average molecular weight (Mn) of less than about 1000 or less than about 900, preferably less than 600, more preferably between about 200 and about 600, and even more preferably between about 400 and about 600. For example, the base coat layer may be formed from a base coat composition that includes a hydrophilic polymer, and PEGDA oligomer dissolved or dispersed in a solvent. The PEGDA may have a Mn of less than about 1000 or less than about 900. In one embodiment, the PEGDA has Mn of less than about 600. In another embodiment, the PEGDA has Mn of between about 200 and about 600. In yet another embodiment, the PEGDA has a Mn of between about 400 and about 600.

The hydrophilic polymer may be, for example, polyvinylpyrrolidone (PVP), polyethylene oxide, methyl cellulose, ethyl cellulose, polyethylene glycol, hydroxyl methylcellulose, hydroxypropyl cellulose, hydroxypropyl methylcellulose, carboxymethyl cellulose, polyvinyl alcohol, or mixtures thereof. In one embodiment, the hydrophilic polymer is a polymer having a Mw above 500,000. For example, the hydrophilic polymer may be PVP having a Mw of at least 500,000. In one embodiment of the base coat composition, the PVP may have a Mw of 1.3 m as determined by light scattering.

The base coat composition may also include a curing agent, such as a photoinitiator, which may be for example a type I photoinitiator, such as Irgacure 2959. The base coat composition also includes a solvent, such as water, ethanol, methanol, isopropyl alcohol, propanol or mixtures thereof. The base coat composition may optionally include additives such as antioxidants or antimicrobials.

In one embodiment, the solid components of the base coat composition in the dry state (without solvent) may include PEGDA in an amount of between about 5 wt % and about 90 wt % of the total solids and a hydrophilic polymer(s) in an amount of between about 10 wt % and about 95 wt % of the total solids. The base coat composition in the dry state may also include a curing agent in the amount of between about 0.1 wt % and about 5 wt % of the total solids. In other embodiments, the solid components in the dry state may include PEGDA in an amount between about 15 wt % and about 25 wt % of the total solids and a hydrophilic polymer(s) in an amount between about 75 wt % and about 85 wt %.

When the solid components are mixed with a solvent to form the base coat composition, the composition may include PEGDA in an amount between about 0.1 wt % and about 5 wt % of the total composition, an amount of hydrophilic polymer(s) of between about 0.5 wt % and about 10 wt %, an amount of solvent of between about 90 wt % and about 99 wt %, and an amount of curing agent of between about 0.01 wt % and about 1 wt %.

In one embodiment, the base coat composition may include:

| | |
|---|---|
| PEGDA | 4.25 g |
| PVP K90 | 0.75 g |
| Irgacure 2959 | 0.2 g |
| Ethanol | 94.8 ml |

In another embodiment, the base coat composition may include:

| | |
|---|---|
| PEGDA | 4.25 g |
| Ethyl Cellulose 10 cP | 0.75 g |
| Irgacure 2959 | 0.2 g |
| Ethanol | 94.8 ml |

In yet another embodiment, the base coat composition may include

| | |
|---|---|
| PEGDA | 4.25 g |
| PVP K90 | 0.50 g |
| Ethyl Cellulose 10 cP | 0.25 g |
| Irgacure 2959 | 0.2 g |
| Ethanol | 94.8 ml |

In another embodiment, the base coat composition may include:

| | |
|---|---|
| PEGDA | 4.25 g |
| Ethyl Cellulose 10 cP | 0.50 g |
| HPM Cellulose | 0.25 g |
| Irgacure 2959 | 0.2 g |
| DI Water | 20.0 ml |
| Ethanol | 74.8 ml |

The base coat layer may be formed on the surface of a medical device by applying the base coat composition to the surface and then curing and/or drying the base coat composition to form the base coat layer. The base coat compositions may be applied in any suitable manner, such as by dip coating or spraying. The base coat composition may be cured and dried by any suitable manner such as by exposure to UV light.

The concentration of the PEGDA in the base coat layer formed from the base coat composition after drying and curing may be less than 85 wt % of the base coat layer. It may also be less than 50 wt % and, in some embodiments, it may be less than 20 wt % of the base coat layer. For example, the base coat layer formed from the composition after drying and curing may include PEGDA in an amount of between about 5 wt % and about 90 wt % of the base coat layer and a hydrophilic polymer in an amount of about 10 wt % and about 95 wt %. In one embodiment, the base coat layer may include PEGDA in an amount between about 80 wt % and about 90 wt % of the base coat layer and the hydrophilic polymer in an amount of between about 10 wt % and about 20 wt % hydrophilic polymer.

Furthermore, the components of the base coat layer may be immiscible or partially immiscible. In one embodiment, the PEGDA of the base coat layer comprises a discrete, continuous or bi-continuous phase within the coating layer. The base coat layer may include a phase separated morphology wherein the PEGDA forms one phase and the hydrophilic polymer forms another phase.

Turning to top coat layer, the top coat layer may be formed from a blend, such as a top coat composition, that is applied over the base coat layer or directly to a treated or untreated surface of a substrate and then cured to form the hydrophilic coating.

In one embodiment of the top coat composition, the composition may include a hydrophilic polymer, and any PEGDA of different Mn described above. These components may be dissolved and/or dispersed in a solvent. The top coat composition may also, optionally, include one or more of curing agents, polyelectrolytes, humectants, plasticizers and/or antioxidants.

The solvent may be any suitable solvent, such as ethanol, methanol, water, isopropyl alcohol or mixtures thereof. Additionally, the PEGDA may have a Mn of less than 1000, or less than 900 or less than 600, or between about 200 and about 600, or between about 400 and about 600.

When used in the top coat composition, the polyelectrolytes may be, for example, a copolymer with acrylic acid, preferably with acrylamide. The polyelectrolyte may be polyacrylic acid-co-acrylamide copolymer (PAAc), polyacrylamide-co-methacrylic acid, or polyacrylic acid. The polyelectrolyte composition may have less than 30% by weight of ionizable groups based on total weight of the copolymer. The humectants or plasticizing agents may be, for example, glycerol or polyethylene glycols or any suitable plasticizer that plasticizes or allows the coating to be more flexible. The curing agent may be a Norrish type I or preferably a Norrish type II photoinitiator, such as benzophenone. The antioxidant may be any suitable antioxidant, such as butyl hydroxytoluene-alcohol (BHT-alcohol).

In one embodiment, the solid components of the top coat composition in the dry state (without solvent) may include PEGDA in an amount of between about 1 wt % and about 20 wt % of the total solids, a hydrophilic polymer(s) in an amount of between about 80 wt % and about 98 wt % and a curing agent in an amount of about 0.05 wt % and about 0.5 wt %. The top coat composition in the dry state may also include an antioxidant in an amount of between about 0.05 wt % and about 0.5 wt % of the total solids, a plasticizer in an amount of between about 2 wt % and about 15 wt %, an polyelectrolyte in an amount of between about 1 wt % and about 10 wt %, and/or any other suitable additive. In other embodiments, the solid components in the dry state may include PEGDA in an amount between about 3 wt % and about 6 wt % of the total solids and a hydrophilic polymer(s) in an amount between about 85 wt % and about 90 wt %, and optionally, an amount of antioxidant, plasticizer, polyelectrolyte and/or any other suitable additive up to 10 wt %.

The top coat composition in the liquid state may include between about 2 wt % and about 10 wt % hydrophilic polymer, between about 0.1 wt % and about 0.6 wt % PEGDA, between about 0.005 wt % and about 0.1 wt % curing agent, and between about 89 wt % and about 97.5 wt % solvent. The top coat composition may, optionally, further include between about 0.005 wt % and about 0.1 wt % antioxidant, between about 0.1 wt % and about 1 wt % plasticizers and/or about 0.1 wt %, about 1 wt % polyelectrolyte and/or any other suitable additive. In another embodiment the top coat in the liquid state may include between 4 wt % and 7 wt % hydrophilic polymer, between 0.2 wt % and 0.4 wt % PEGDA between about 0.005 wt % and 0.015 wt % curing agent and about 90 wt % to 95 wt % solvent and optionally, an amount of antioxidant, plasticizer, polyelectrolyte and/or any other suitable additive.

The top coat composition may be applied over the base coat layer or directly to the treated or untreated surface of the medical device in any suitable manner, such as by dip coating or spraying. The top coat composition may then be cured in any suitable manner to form the top coat layer and the hydrophilic coating. For example, curing of the top coat composition may include curing by exposure to UV light.

In one embodiment, the dried and/or cured top coat layer formed from the composition may include about 80 wt % to about 95.5 wt % hydrophilic polymer and about 0.5 wt % to about 20 wt % PEGDA. The top coat layer may optionally include about 1 wt % to about 10 wt % plasticizer and/or about 1 wt % to about 10 wt % polyelectrolyte. In one embodiment, the top coat layer may include hydrophilic polymer in an amount between about 94 wt % to about 98 wt %, PEGDA in an amount between about 2 wt % to about 6 wt % and, optionally, an amount of antioxidant, plasticizer, polyelectrolyte and/or any other suitable additive.

The components of the top coat layer may be immiscible or partially immiscible. For example, the PEGDA of the top coat layer may be a partially immiscible or an immiscible component. In one embodiment, the PEGDA of the top coat layer comprises a discrete, continuous or bi-continuous phase within the coating layer. The top coat layer may include a multiple phase morphology wherein the PEGDA separates from the hydrophilic polymer phase during drying and curing. That is, wherein the PEGDA forms one phase and the hydrophilic polymer forms a second phase.

To form the lubricious hydrophilic coating on a substrate, such as a medical device, the base coat composition, when one is used, is applied to a surface of the substrate, by for example, dip coating, spraying or any other suitable manner. The base coat is then cured and/or dried by, for example, UV lights or any other suitable manner. In one embodiment, curing and drying the base coat composition results in a base coat layer having a multiple-phase morphology. The top coat composition is then applied over the base coat layer, when one is used, or applied directly to the treated or untreated surface of the substrate by, for example, dip coating, spraying or any other suitable manner. The top coat composition is then cured and/or dried to form the top coat layer. Curing and/or drying can be done by, for example, exposure to UV light or any other suitable manner. In one embodiment, curing and/or drying of the top coat composition results in a top coat having phase separated components.

When the coating is formed, the substrate may be packaged in a wet environment wherein the substrate is in direct liquid contact with a wetting fluid containing one or more non-polymeric polyols. The package containing the medical device and the wetting fluid, optionally, may be radiation sterilized by, for example, gamma or E-beam radiation.

EXAMPLES

Example 1

Hydrophilic coatings were formed on the outer surfaces of catheters made from polyvinyl chloride (PVC catheters). The catheters had a size of CH14 and a shore hardness of 82A. The hydrophilic coatings included a base coat layer formed on the outer surface of the catheter and a top coat layer formed over the base coat layer.

Base Coat Composition

The base coat composition was prepared with the components as shown in the table below.

TABLE 1

| Component | Amount |
|---|---|
| Methanol | 97.98% (w/w) |
| Polyvinylpyrrolidone K90 (PVP) (Ashland) | 1.61% (w/w) |
| Irgacure 2959 (BASF) | 0.01% (w/w) |
| Polyethylene glycol diacrylate (PEG400DA) (SR344, Sartomer, inhibitor removed) | 0.40% (w/w) |

The base coat composition was prepared by slowly adding the PVP to methanol while mixing until the PVP was dissolved. PEG400DA and Irgacure 2959 were then added and allowed to fully dissolve while the solution was stirred.

Top Coat Composition

The top coat composition was prepared with the components as shown in the table below.

TABLE 2

| Component | Amount (w/w) |
|---|---|
| Ethanol (absolute) (Lennox) | 78.99% (w/w) |
| De-ionized water (Lennox) | 14.00% (w/w) |
| PVP K90 (Ashland) | 5.95% (w/w) |
| BHT-A (Sigma Aldrich) | 0.01% (w/w) |
| PEG400DA (SR344, Sartomer, inhibitor removed) | 0.30% (w/w) |
| Glycerol | 0.74% (w/w) |
| Benzophenone | 0.01% (w/w) |

The top coat composition was prepared by adding PVP to the ethanol and water and mixing until dissolved. The remaining components (glycerol, PEG400DA, BHT-A, and benzophenone) were then added and allowed to fully dissolve under stirring.

To form the hydrophilic coating on the outer surfaces of the catheters, the catheters were immersed in the base coat composition for a period of 10 seconds and then withdrawn at a rate of 0.7 cm/sec using a Harland PCX coating machine containing UV lamps. The base coat composition was then cured and dried under UV lamps for 45 seconds to form a base coat layer on the outer surface of the catheter. The catheters were then immersed in the top coat composition for 10 seconds and withdrawn at a rate of 0.5 cm/sec. The top coat composition was then UV cured and dried under UV lamps for 10 minutes to form the top coat layer, (resulting in the formation of the hydrophilic coating on the catheter).

After the hydrophilic coating was formed on each of the catheters, the catheters were individually packaged and sealed in foil packs containing 5 ml of wetting fluid wherein the wetting fluid included 89.6 wt % water, 10 wt % glycerol and 0.4 wt % ascorbic acid. One set (Sample Set A) of the foil packs was exposed to 45 kGy of E-Beam radiation and another set (Sample Set B) was exposed to 35 kGy of E-Beam radiation.

The packages were opened and the catheters were removed from the packages and the initial, abraded and ten minute dry-out coefficients of friction (CoFs) of catheters were a tested.

CoF measurements are an indicator of lubricity and were measured using a Harland Friction Tester Model FTS5500. The CoFs of the catheters were determined by inserting a mandrel into 127 mm section of the coated catheter tube. The tube was then clamped between two pieces of silicone rubber at 100 g load wherein the silicone rubber had a shore hardness of 60A. The catheter tube with the mandrel inserted therein was pulled through the two pieces of silicone rubber at a speed of 10 mm/s. The force required to pull about 80 mm of the catheter tube through the two pieces of silicone rubber was measured. The CoF value was calculated from the ratio of recorded to applied loads (i.e., the recorded load divided by the applied load) when steady state was reached. The CoF of each type of catheter was measured immediately after opening the package ("initial"), immediately after being abraded ("abraded") and immediately after a ten-minute dry-out time ("dry-out").

In measuring the abraded CoFs, the catheter, with the hydrophilic coating in a hydrated state, was cycled back and forth 25 times through a hole in a 1 mm thick, silicone pad having a shore hardness of 60A. The hole was just smaller than the outer diameter of the catheter tube and the abrasion took place under water. Abrading the catheter in this fashion is designed to remove any portions of the coating that is not well adhered to the tubes. After abrasion, the CoF was measured as described above.

In measuring the ten minute dry-out time CoF, the catheter, immediately after removal from the package was placed in an atmosphere having a temperature of 23° C. and a relative humidity of 50% for 10 minutes before measuring the CoF as described above.

Example 1 Results

Coefficient of Friction Measurements

Table 3 shows the average CoFs for the initial, abraded and ten-minute dry-out CoFs for each set of catheters.

TABLE 3

| Sample Set | E-Beam Radiation Dose | Initial CoF Avg. | Abraded CoF Avg. | 10 Min Dry-out Avg. |
|---|---|---|---|---|
| A | 45 kGy | 0.012 | 0.018 | 0.027 |
| B | 35 kGy | 0.014 | 0.016 | 0.018 |

Example 2

The hydrophilically coated catheters of Example 2 were coated with the same base and top coats as described in Example 1 and by the same coating procedures. After the hydrophilic coating was formed on each of the catheters, the catheters were individually packaged and sealed within a foil pack containing 5 ml a wetting fluid. The wetting fluid was one of following:

TABLE 4

| Wetting Fluid Sample | Wetting Fluid Components |
|---|---|
| C | 100% deionized water (DI water) |
| D | 99 wt % DI water: 1 wt % Ascorbic Acid |
| E | 90 wt % DI water: 10 wt % Ascorbic Acid |
| F | 89.6 wt % DI water: 10 wt % Glycerol: 0.4 wt % Ascorbic Acid |

After the packages were sealed, the packages were exposed to a dose of about 30-35 kGy of gamma radiation. The packages were then opened and the catheters were removed from the packages and the initial and abraded CoFs of catheters were a tested using the above described procedures.

Example 2 Results

Coefficient of Friction Measurements

Table 5 shows the average CoFs for the initial and abraded CoFs for each set of catheters.

TABLE 5

| Wetting Fluid Sample | Initial CoF Avg. | Abraded CoF Avg. |
|---|---|---|
| C | 0.013 | 0.104 |
| D | 0.030 | 0.264 |
| E | 0.012 | 0.064 |
| F | 0.016 | 0.027 |

Dye uptake tests were conducted on the catheters to assess the level of adhesion/non-adhesion between the hydrophilic coatings and catheters. After the CoFs of the abraded catheters were measured, the catheters were dried-out (dehydrate). The dried-out catheters were then immersed in a water soluble red dye for 2 minutes. The catheters were then visually inspected to determine if the dye had been uniformly taken up throughout the coating or if sections of the coated portion of the catheter were dye-free. A uniform dye uptake throughout the coated portion of the catheter indicates that the hydrophilic coating has good adhesion to the catheter. If the coated portion of the catheter has undyed sections, this is an indication that the hydrophilic coating or sections thereof have significantly thinned and/or separated from the catheter due to lack of adhesion to the catheter.

FIG. 1 shows the results of dye test conducted on the abraded catheters that were wetted with Wetting Fluid Samples C-F.

Example 3

The surfaces of catheter tubes made of thermoplastic elastomer (TPE) with a 83 shore hardness were coated with the lubricious top coat formation and top coat application process as described in Example 1 without the use of a base coat or surface treatment being applied to the catheter tube surface prior to coating, i.e., the surface of the catheter tube did not undergo any plasma treatment, corona treatment or the like or any surface cleaning with a solvent prior to applying the top coat formulation. The coated catheter tubes were placed into foil pouches containing 5 mL of wetting fluid. The wetting fluid included 89.6 wt % water, 10 wt % glycerol and 0.4 wt % vitamin C. After ten days, the catheter tubes were sterilized using e-beam radiation at a dose of 45 KGy. The sterilized catheter tubes were removed from the foil pouches the initial, dry out and abraded Cofs were measured.

Dye uptake tests were conducted on the catheters to assess the level of adhesion/non-adhesion between the hydrophilic coatings and catheters. After the CoFs of the abraded catheters were measured, the catheters were dried-out (dehydrate). The dried-out catheters were then immersed in a water soluble red dye for 2 minutes. The catheters were then visually inspected to determine if the dye had been uniformly taken up throughout the coating or if sections of the coated portion of the catheter were dye-free. A uniform dye uptake throughout the coated portion of the catheter indicates that the hydrophilic coating has good adhesion to the catheter. If the coated portion of the catheter has undyed sections, this is an indication that the hydrophilic coating or sections thereof have significantly thinned and/or separated from the catheter due to lack of adhesion to the catheter.

Example 3 Results

Coefficient of Friction Measurements

Table 6 shows the average CoFs for the initial, abraded and ten-minute dry-out CoFs for catheters of Example 3.

TABLE 6

| Initial CoF Avg. | Abraded CoF Avg. | 10 Min Dry-out Avg. |
|---|---|---|
| 0.015 | 0.020 | 0.032 |

Figure 2:
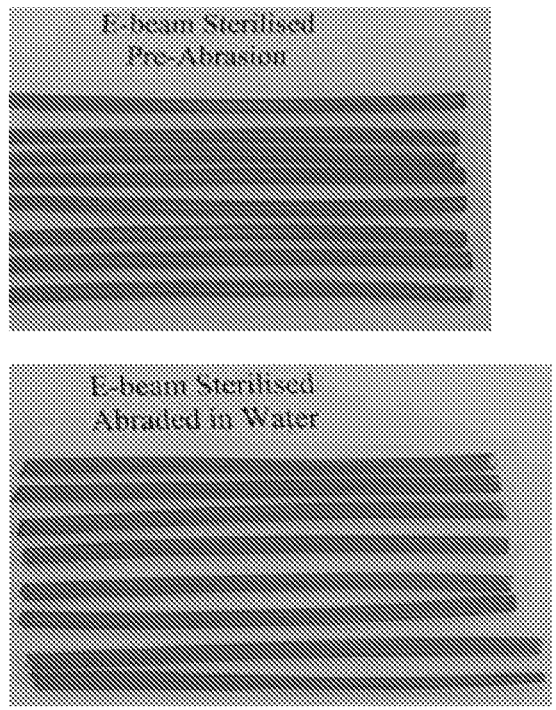
FIG. 2 includes photographs of catheter tubes showing the visual results of the dye test of Example 3.

FIG. 2 shows the results of dye test conducted on the catheters tubes of Example 3.

Comparative Example 1

The surfaces of catheter tubes made of thermoplastic elastomer (TPE) with a 83 shore hardness were coated with the below lubricious top coat formation without the use of a base coat or surface treatment being applied to the catheter tube surface prior to coating. The top coat formation was applied using the same top coat application process as described in Example 1.

TABLE 7

| Component | Amount (grams) |
|---|---|
| PVP K90 (Ashland) | 13 g |
| Glycerol | 0.8 g |
| Esacure one (Lamberti) | 0.13 g |
| Ethanol/Water Mixture 85:15 by weight | 215 g |

The coated catheter tubes were placed into foil pouches containing 5 mL of wetting fluid. The wetting fluid included 89.6 wt % water, 10 wt % glycerol and 0.4 wt % vitamin C. After ten days, the catheter tubes were sterilized using e-beam radiation at a dose of 45 KGy. The sterilized catheter tubes were removed from the foil pouches the initial, dry out and abraded Cofs were measured.

Dye uptake tests were conducted on the catheters to assess the level of adhesion/non-adhesion between the hydrophilic coatings and catheters. After the CoFs of the abraded catheters were measured, the catheters were dried-out (dehydrate). The dried-out catheters were then immersed in a water soluble red dye for 2 minutes. The catheters were then visually inspected to determine if the dye had been uniformly taken up throughout the coating or if sections of the coated portion of the catheter were dye-free. A uniform dye uptake throughout the coated portion of the catheter indicates that the hydrophilic coating has good adhesion to the catheter. If the coated portion of the catheter has undyed sections, this is an indication that the hydrophilic coating or sections thereof have significantly thinned and/or separated from the catheter due to lack of adhesion to the catheter.

Comparative Example 1 Results

Coefficient of Friction Measurements

Table 8 shows the average CoFs for the initial, abraded and ten-minute dry-out CoFs for catheters of Comparative Example 1.

TABLE 8

| Initial CoF Avg. | Abraded CoF Avg. | 10 Min Dry-out Avg. |
|---|---|---|
| 0.038 | 0.126 | 0.024 |

Figure 3:
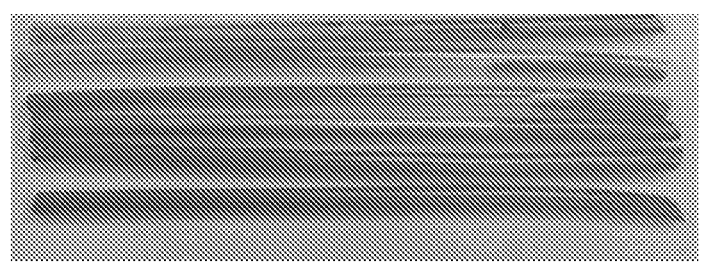
FIG. 3 includes a photograph of catheter tubes showing the visual results of the dye test of Comparative Example 1.

FIG. 3 shows the results of dye test conducted on the abraded catheters tubes of Comparative Example 1. The sterilized coatings of Comparative Example 1 showed a degradation of the coating performance after hydration and eBeam sterilization at 45 KGy following abrasion.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A method for sterilizing a medical device comprising a substrate having a hydrophilic coating, said method comprising:
    contacting the hydrophilic coating of the substrate with a wetting fluid containing one or more non-polymeric polyols, the hydrophilic coating including a hydrophilic polymer and low molecular diacrylate; and
    sterilizing the medical device by applying a sufficient amount of radiation while the device is in contact with the wetting fluid.

2. The method of claim 1 wherein the medical device comprises a urinary catheter.

3. The method of claim 1 wherein the one or more non-polymeric polyols comprises one or more of Glycerol, Erythritol, Threitol, Arabitol, Xylitol, Adonitol, Mannitol, Sorbitol, Galactitol, Fucitol, Iditol, Inositol, Volemitol, Isomalt, Maltitol, Lactitol, Maltotriitol, and Maltotetraitol.

4. The method of claim 1 wherein the one or more non-polymer polyols comprises Glycerol.

5. The method of claim 1 wherein the one or more non-polymeric polyols is between about 5 wt % and about 50 wt % of the wetting fluid.

6. The method of claim 1 wherein the one or more non-polymeric polyols is between about 10 wt % and about 20 wt % of the wetting fluid.

7. The method of claim 1 wherein the one or more non-polymeric polyols is about 5 wt % of the wetting fluid.

8. The method of claim 1 wherein the low molecular diacrylate comprises polyethylene glycol diacrylate.

9. The method of claim 8 wherein the number average molecular weight of the polyethylene glycol diacrylate is less than about 600.

10. The method of claim 9 wherein the polyethylene glycol diacrylate has a number average molecular weight between about 200 and about 600.

11. The method of claim 9 wherein hydrophilic coating comprises about 80 wt % to about 95.5 wt % hydrophilic polymer and about 0.5 wt % to about 20 wt % polyethylene glycol diacrylate.

12. The method of claim 9 wherein the hydrophilic coating comprises about 94 wt % to about 98 wt % hydrophilic polymer and about 2 wt % to about 6 wt % polyethylene glycol diacrylate.

13. The method of claim 9 wherein the hydrophilic coating comprises a polyethylene glycol diacrylate as a partially immiscible or an immiscible component.

14. The method of claim 9 wherein the polyethylene glycol diacrylate comprises a discrete, continuous or bi-continuous phase within the coating.

15. A medical device assembly comprising:
    a package defining a cavity;
    a medical device including a hydrophilic coating located within the cavity, the hydrophilic coating including a hydrophilic polymer and low molecular diacrylate; and
    a wetting fluid comprising one or more non-polymeric polyols located within the cavity and in contact with the hydrophilic coating.

16. The assembly of claim 15 wherein the medical device comprises a urinary catheter.

17. The assembly of claim 16 wherein the one or more non-polymeric polyols comprises one or more of Glycerol, Erythritol, Threitol, Arabitol, Xylitol, Adonitol, Mannitol, Sorbitol, Galactitol, Fucitol, Iditol, Inositol, Volemitol, Isomalt, Maltitol, Lactitol, Maltotriitol, and Maltotetraitol.

18. A method of forming an irradiation sterilized urinary catheter, comprising:
    applying a hydrophilic coating to an untreated surface of a urinary catheter;
    contacting the hydrophilic coating of the urinary catheter with a wetting fluid containing one or more non-polymeric polyol; and
    sterilizing the urinary catheter by applying a sufficient amount of radiation while the urinary catheter is in contact with the wetting fluid.

19. The method of claim 18 wherein the hydrophilic coating comprises a hydrophilic polymer and a low-molecular weight PEGDA.

20. The method of claim 18 wherein the one or more non-polymeric polyol comprises one or more of Glycerol, Erythritol, Threitol, Arabitol, Xylitol, Adonitol, Mannitol, Sorbitol, Galactitol, Fucitol, Iditol, Inositol, Volemitol, Isomalt, Maltitol, Lactitol, Maltotriitol, and Maltotetraitol.

* * * * *